United States Patent
Tsutsumi

(10) Patent No.: US 8,578,727 B2
(45) Date of Patent: Nov. 12, 2013

(54) INDOOR UNIT AND AIR-CONDITIONING APPARATUS PROVIDED WITH THE SAME

(75) Inventor: Hiroshi Tsutsumi, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 723 days.

(21) Appl. No.: 12/808,297

(22) PCT Filed: Mar. 21, 2008

(86) PCT No.: PCT/JP2008/055214
§ 371 (c)(1),
(2), (4) Date: Jun. 15, 2010

(87) PCT Pub. No.: WO2009/116160
PCT Pub. Date: Sep. 24, 2009

(65) Prior Publication Data
US 2010/0293976 A1    Nov. 25, 2010

(51) Int. Cl.
*F25B 49/00* (2006.01)
*F25B 41/04* (2006.01)

(52) U.S. Cl.
USPC .......................................... 62/176.6; 62/223

(58) Field of Classification Search
USPC ............. 62/176.6, 527, 228.1, 222, 223, 125, 62/129
See application file for complete search history.

(56) References Cited

FOREIGN PATENT DOCUMENTS

| JP | 4-015457 A | 1/1992 |
|---|---|---|
| JP | 4-113136 A | 4/1992 |
| JP | 10-227508 A | 8/1998 |
| JP | 2001-033078 A | 2/2001 |
| JP | 2001-033079 A | 2/2001 |
| JP | 2003-130430 A | 5/2003 |
| JP | 2006-090597 A | 4/2006 |
| JP | 2006-118822 A | 5/2006 |

OTHER PUBLICATIONS

International Search Report dated Jun. 10, 2008.
Chinese Office Action dated Aug. 3, 2012, with English-language translation.
Office Action issued Mar. 18, 2013 in corresponding Chinese Patent Application No. 200880125286.9, and an English translation thereof.
Office Action (Notification of the third Office Action) issued Aug. 9, 2013 in corresponding Chinese Patent Application No. 200880125286.9, and an English translation thereof.

*Primary Examiner* — Chen Wen Jiang
(74) *Attorney, Agent, or Firm* — Buchanan Ingersoll & Rooney PC

(57) ABSTRACT

To provide a low-cost and highly reliable indoor unit and an air-conditioning apparatus having the same by obtaining a dew point temperature at the outlet side without installing a humidity sensor and a dew point temperature detector at the outlet side. An indoor unit includes: an evaporator, a blower, a suction air temperature detector that detects a suction air temperature at the upstream side of an air flow of the evaporator, an outlet air temperature detector that detects an outlet air temperature at the downstream side of the air flow of the evaporator, an evaporator inlet fluid temperature detector that detects a fluid temperature at the fluid inlet side of the evaporator, an adjustment valve that adjusts a flow amount of the fluid made to flow into the evaporator, and a controller that calculates a suction air dew point temperature by suction air temperature information detected by the suction air temperature detector to calculate an outlet air dew point temperature based on the suction air dew point temperature, the suction air temperature, the outlet air temperature, and the evaporator inlet piping temperature.

19 Claims, 14 Drawing Sheets

| CONDITIONS | CONTROL OPERATION |
|---|---|
| $3 < \Delta T$ | $Lj1 = Lj0 + 3$ |
| $1 < \Delta T \leq 3$ | $Lj1 = Lj0 + 1$ |
| $-1 < \Delta T \leq 1$ | $Lj1 = Lj0$ |
| $-3 < \Delta T \leq -1$ | $Lj1 = Lj0 - 1$ |
| $\Delta T \leq -3$ | $Lj1 = Lj0 - 3$ |

Lj1 : NEW ADJUSTMENT VALVE OPENING DEGREE
Lj0 : CURRENT ADJUSTMENT VALVE OPENING DEGREE

OUTLET AIR DEW POINT TEMPERATURE
Tdout=Tdin-(Tin-Tout)*(Tdin-Tpin-K)/(Tin-Tpin-K)
Tdin : SUCTION DEW POINT TEMPERATURE
Tpin: PIPING TEMPERATURE
Tin: SUCTION TEMPERATURE
Tout: OUTLET TEMPERATURE
K: COMPENSATION COEFFICIENT (a) (b)

IN THE CASE OF LARGE FLOW AMOUNT
(a)

IN THE CASE OF SMALL FLOW AMOUNT
(b)

(a)  (b)

F I G. 1 5
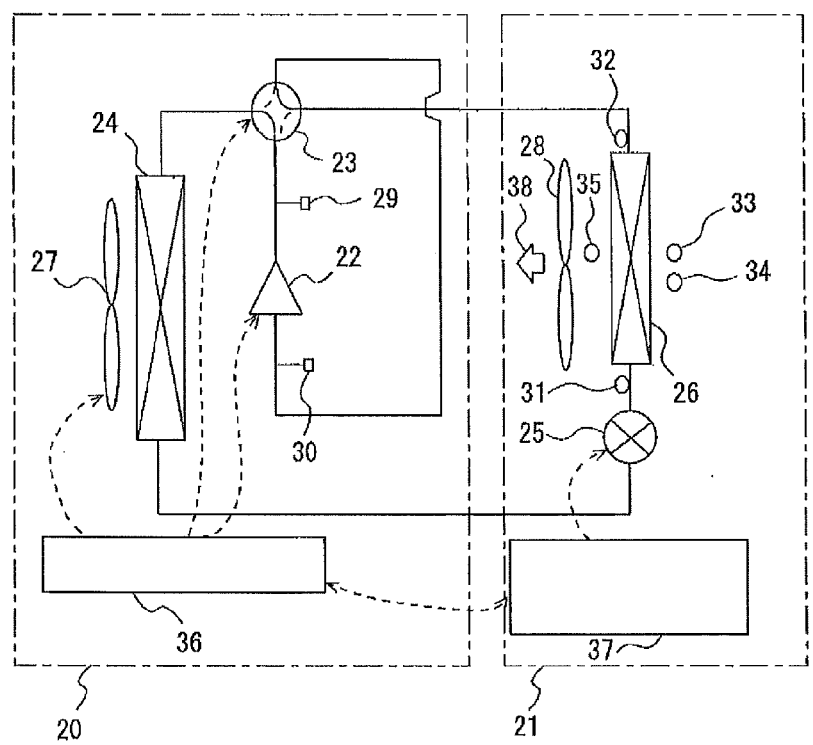

S : DIFFERENCE BETWEEN Tpout AND Tpin
Tpin : LIQUID SIDE PIPING TEMPERATURE
Tpout : GAS SIDE PIPING TEMPERATURE
Sm : TARGET VALUE OF "S"
$\Delta$Lj : REDUCING AMOUNT OF THROTTLE DEVICE
Lj : OPENING DEGREE OF THROTTLE DEVICE
Ljmax : MAXIMUM OPENING DEGREE OF THROTTLE DEVICE
Ljmin : MINIMUM OPENING DEGREE OF THROTTLE DEVICE (*) INDOOR UNIT OUTLET AIR DEW POINT TEMPERATURE
= REHEAT UNIT OUTLET AIR DEWPOINT TEMPERATURE

INDOOR UNIT AND AIR-CONDITIONING APPARATUS PROVIDED WITH THE SAME

TECHNICAL FIELD

The present invention relates to an indoor unit that controls a dew point temperature of the air (hereinafter, refer to as outlet air) blown out from the indoor unit to an air-conditioning subject area and an air-conditioning apparatus provided with the same; more particularly to the indoor unit that calculates the dew point temperature of the outlet air without using a dew point temperature detector and the air-conditioning apparatus provided with the same.

BACKGROUND ART

Conventionally, there is an air-conditioning apparatus that can control a dew point temperature of an outlet air. In such an air-conditioning apparatus, a dew point temperature detector or a humidity sensor are generally installed at an outlet to control the dew point temperature of the outlet air to be constant. As such, "a clean room using a direct expansion heat exchanger, in which the dew point temperature of the brought-in outer air is adjusted by the rotation frequency control of a compressor in the heat pump apparatus so that a detected value of a dew point sensor installed at an air cooler side is within a predetermined range" is proposed. (For example, refer to Patent Document 1)

Patent Document 1

Japanese Unexamined Patent Application Publication No. H04-113136 (FIG. 2)

SUMMARY OF INVENTION

Problems to be Solved by the Invention

When using a dew point temperature detector (dew point sensor) like a technique described in Patent Document 1, a problem exists that the dew point temperature detector is usually expensive, resulting in high cost. Another problem is that because maintenance of the dew point temperature detector is difficult, maintenance operation is troublesome. Furthermore, although a humidity detector is easily available at lower cost, since a relative humidity sometimes becomes 100% when used in an outlet, problems resulting in false detection and reduction in life expectancy occur such that an inexpensive humidity detector becomes out-of-service, and dew condensation occurs in the humidity detector when operation of the air-conditioning apparatus is unstable.

The present invention is made to solve the problems above. The purpose of the present invention is to provide a low-cost and highly reliable indoor unit and the air-conditioning apparatus having the same by obtaining a dew point temperature at an outlet without installing a humidity sensor and a dew point temperature detector at the outlet.

Means for Solving the Problems

An indoor unit according to the present invention includes: an evaporator, a blower that supplies air to the evaporator, a suction air temperature detector that detects a suction air temperature at the upstream of the air flow of the evaporator, an outlet air temperature detector that detects an outlet air temperature at the downstream of the air flow of the evaporator, an evaporator inlet fluid temperature detector that detects a fluid temperature at the fluid inlet of the evaporator, an adjustment valve that adjusts the flow amount of the fluid made to flow into the evaporator, and a controller that calculates a suction air dew point temperature by suction air temperature information detected by the suction air temperature detector to calculate an outlet air dew point temperature based on the suction air dew point temperature, the suction air temperature, the outlet air temperature, and the evaporator inlet piping temperature.

With the air-conditioning apparatus according to the present invention, a heat source unit with a compressor being mounted is connected with the above indoor unit. It is characterized in that the controller controls a drive frequency of the compressor so that the calculated outlet dew point temperature reaches a predetermined target value.

Effect of the Invention

With the gas indoor unit and the air-conditioning apparatus according to the present invention, an outlet dew point temperature can be obtained without installing a humidity sensor and a dew pint temperature detector at the air outlet of the indoor unit, therefore, not only low-cost manufacturing is achieved but also reliability can be improved.

BRIEF DESCRIPTION OF DRAWINGS

FIG. 15 is a circuit configuration diagram showing the schematic circuit configuration of the air-conditioning apparatus according to Embodiment 4.

DESCRIPTIONS OF CODES AND SYMBOLS

Figure 1:
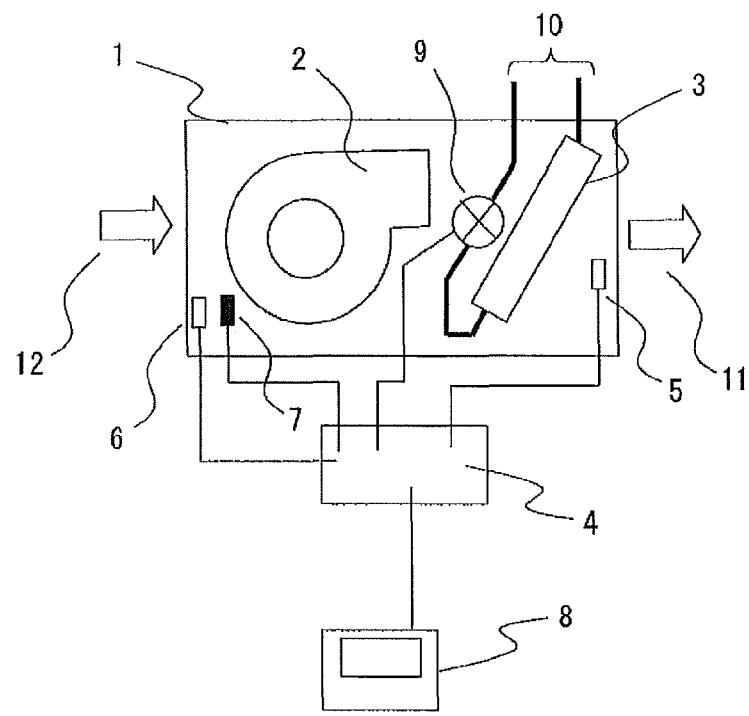
FIG. 1 is an internal configuration diagram illustrating a schematic internal configuration of the indoor unit of the air-conditioning apparatus according to Embodiment 1.

1 indoor unit
2 blower
3 evaporator
4 controller
5 outlet air temperature detector
6 suction air temperature detector
7 suction air humidity detector
8 remote controller
9 adjustment valve
10 piping
11 outlet air
12 suction air
14 evaporator inlet fluid temperature detector
15 evaporator outlet piping temperature detector
20 heat source unit
21 indoor unit
22 compressor
23 four-way valve
24 heat source side heat exchanger
25 throttle device
26 indoor unit side heat exchanger
27 heat source side blower
28 indoor unit side blower
29 high-pressure pressure detector
30 low-pressure pressure detector
31 liquid-side piping temperature detector
32 gas-side piping temperature detector
33 suction air temperature detector
34 suction air humidity detector
35 outlet air temperature detector
36 heat source unit side controller
37 indoor unit side controller
38 outlet air
40 condenser
41 adjustment valve
42 outlet air temperature detector
43 controller
44 piping
45 reheat unit
100 air-conditioning apparatus

BEST MODE FOR CARRYING OUT THE INVENTION

Descriptions will be given to embodiments of the present invention based on drawings as follows.

Embodiment 1

FIG. 1 is an internal configuration diagram illustrating a schematic internal configuration of the indoor unit of the air-conditioning apparatus according to Embodiment 1. Descriptions will be given to the internal configuration and operation of the indoor unit 1 will be given based on FIG. 1. The air-conditioning apparatus performs cooling operation or heating operation utilizing a refrigeration cycle (heat pump cycle) circulating a refrigerant. In FIG. 1, a controller 4 and a remote controller 8 are illustrated in combination. An outlet air 11 and a suction air (mainly outdoor air) 12 are illustrated in combination, as well. Including FIG. 1, the size relation of each component may be different from actuality in the following drawings.

The air-conditioning apparatus according to Embodiment 1 is largely composed of the indoor unit 1 and a heat source unit (not shown). The indoor unit 1 and heat source unit are connected and communicated by piping 10. In the indoor unit 1, a blower 2, an evaporator 3, an outlet air temperature detector 5, a suction air temperature detector 6, a suction air humidity detector 7, and an adjustment valve 9 are mainly mounted. Detected information by the outlet air temperature detector 5, the suction air temperature detector 6, the suction air humidity detector 7 and commands from the user to be transferred via a remote controller 8 are arranged to be transmitted to a controller 4. In addition, in Embodiment 1, cooling operation will be mainly explained, and at the time of heating operation, the evaporator 3 operates as a condenser.

On the other hand, in the heat source unit (outdoor unit, not shown), a compressor, a condenser, and outdoor blower are mainly mounted. Then, the compressor, the condenser, the adjustment valve 9, and the evaporator 3 are connected in series by piping 10 to form a refrigerant circuit. Cooling operation or heating operation of the air-conditioning apparatus is executed by the circulation of the refrigerant in the refrigerant circuit. An example is shown, in which the controller 4 is provided outside of the indoor unit 1, however, the controller 4 may be provided in the indoor unit 1. Moreover, connection conditions among the controller 4, each detector, and remote controller 8 are denoted by solid lines, however, they may be either wired or wireless. Detailed descriptions on the heat source unit will be given in Embodiment 4.

Functions of each apparatus mentioned above will be explained. The indoor unit 1 is installed in an air-conditioning subject apparatus (a room, a server room, and the like). The air for air-conditioning (here, outlet air for cooling operation) is outlet to an air-conditioning subject area. The blower 2 has a function to take in a suction air 12 into the indoor unit 1 to supply it to the evaporator 3 and to blow out the air passed through the evaporator 3 toward the outside of the indoor unit 1 as the outlet air 11. The evaporator 3 performs heat exchange between the air supplied from the blower 2 and the refrigerant conducting through piping 10 to turn the refrigerant into an evaporation gas. (Detailed descriptions will be given in FIG. 2) The adjustment valve 9 decompresses the refrigerant to expand it. It may be composed by an opening-degree-variably-controllable valve such as an electronic expansion valve (LEV).

The outlet air temperature detector 5 is installed in the vicinity of the outlet of the indoor unit 1, and detects the temperature of the outlet air 11 to transmit the detected temperature to the controller 4. The suction air temperature detector 6 is installed in the vicinity of the inlet of the indoor unit 1, and detects the temperature of the suction air 12 to transmit the detected temperature to the controller 4. The suction air humidity detector 7 is installed in the vicinity of the inlet of the indoor unit 1, and detects the humidity of the suction air 12 to transmit the detected humidity to the controller 4. The controller 4 is composed of such as a microcomputer and arranged to control the opening degree of the adjustment valve 9 based on detected information by the outlet air temperature detector 5, the suction air temperature detector 6, and the suction air humidity detector 7 and commands from the remote controller 8. The remote controller 8 receives directions from the user.

The heat source unit may be any of only for cooling operation or cooling-operation heating-operation switchable, a multi-type of connecting a plurality of indoor units, a type capable of simultaneous operation of cooling operation and heating operation, and the like. A form of operation is not limited in particular. A fluid flowing into the evaporator 3 (a fluid conducting piping 10 to circulate in the refrigeration cycle) may be a refrigerant such as R410A and may be water and brine, and the like. For the refrigerant such as R410A, the adjustment valve 9 acts as a throttle device. For water, brine, and so on, the adjustment valve 9 acts as a flow amount adjusting valve. In any case, the adjustment valve 9 can electrically adjust a valve opening degree.

Figure 2:
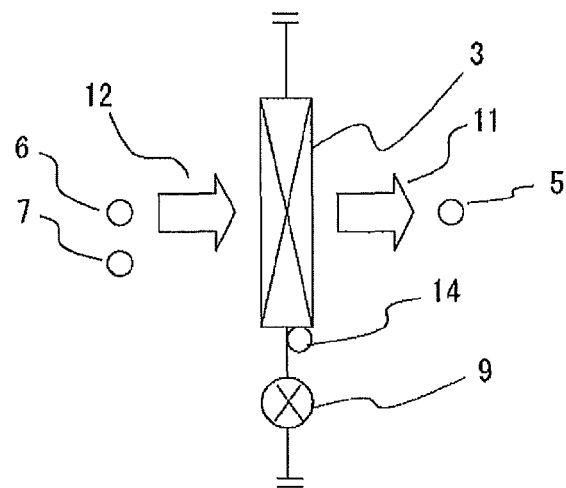
FIG. 2 is an illustrative drawing that illustrates an evaporator in detail.

FIG. 2 is an illustrative drawing that illustrates the evaporator 3 in detail. The evaporator 3 will be explained in detail based on FIG. 2 along with a diagrammatic arrangement of the temperature detector related to the evaporator 3. The suction air temperature detector 6 and the suction air humidity detector 7 are installed, as mentioned above, in the vicinity of the inlet of the indoor unit 1, that is, at the upstream of the air flow of the evaporator 3. The outlet air temperature detector 5 is installed, as mentioned above, in the vicinity of the outlet of the indoor unit 1, that is, at the downstream of the air flow of the evaporator 3. At the fluid inlet of the evaporator 3, the evaporator inlet fluid temperature detector 14 is installed to detect the fluid temperature conducting in piping 10 at the inlet of the evaporator 3.

Here, a dry bulb temperature of the suction air temperature detector 6 is a detected dry bulb temperature Tin. Detected humidity by the suction air humidity detector 7 is detected humidity Hin. Detected temperature by the outlet air temperature detector 5 is detected temperature Tout. Detected temperature of the evaporator inlet fluid temperature detector 14 is detected temperature Tpin. They will be used in the following descriptions. Each dew point temperature Tdin, detected temperature Tout, and detected temperature Tpin calculated from the detected dry bulb temperature Tin, and the detected humidity Hin is used in an open degree control of the adjustment valve 9 in the controller 4. (Detailed descriptions will be given in the flowchart shown in FIG. 4.)

The outlet air temperature detector 5 is arranged to be installed at a location where the temperature of an average outlet air 11 can be detected in the vicinity of the outlet of the indoor unit 1. The evaporator inlet fluid temperature detector 14 is arranged to be installed at a location where as low temperature as possible can be detected in the fluid temperature conducting in piping 10 at the inlet of the evaporator 3. In the operation using a refrigerant, since the temperature changes by a pressure loss in the piping 10, when using a distributor having a large pressure loss, the evaporator inlet fluid temperature detector 14 is arranged to be installed just before the inlet of the evaporator 3 at the downstream of the distributor.

Next, operation of the indoor unit 1 will be explained. When the indoor unit 1 starts operation, a high-temperature and humidity suction air 12 sucked by the indoor unit 1 is cooled and dehumidified by the evaporator 3 to be turned into low-temperature outlet air 11 and blown out into an air-conditioning subject area. Here, the evaporator 3 is connected with the heat source unit and the adjustment valve 9 by the piping 10 and cooling performance adjustment is performed by the adjustment valve 9. The cooling performance control is executed by deciding a target value by the input mainly from the remote controller 8.

Namely, a target indoor dry bulb temperature Tm is set by the remote controller 8. Based on the target indoor dry bulb temperature Tm and 50% of a pre-stored relative humidity target value, a target dew point temperature Tdm is calculated by the controller 4. The target dew point temperature Tdm is preprogrammed in the controller 4 to be converted based on a humidity psychrometric diagram. The relative humidity target value pre-stored in the controller 4 can be changed by selecting values among 40%, 45%, 50%, 55%, and 60% by a switching operation by such as switches. The user can arbitrarily set the humidity by using the remote controller 8 having a humidity input function. An input from the remote controller 8 may be the target dew point temperature Tdm instead of the target indoor dry bulb temperature Tm.

In order to control the adjustment valve 9, using the target dew point temperature Tdm and a outlet air dew point temperature Tdout, the controller 4 obtains a difference $\Delta T = Tdout - Tdm$ to adjust the adjustment valve 9 according to the results. That is, the controller 4 controls the opening degree of the adjustment valve 9 to increase when $\Delta T$ is positive, and to decrease when negative. Here, opening degree control operation according to $\Delta T$ calculated by the controller 4 will be explained while referring to FIG. 3.

Figures 3, 4:
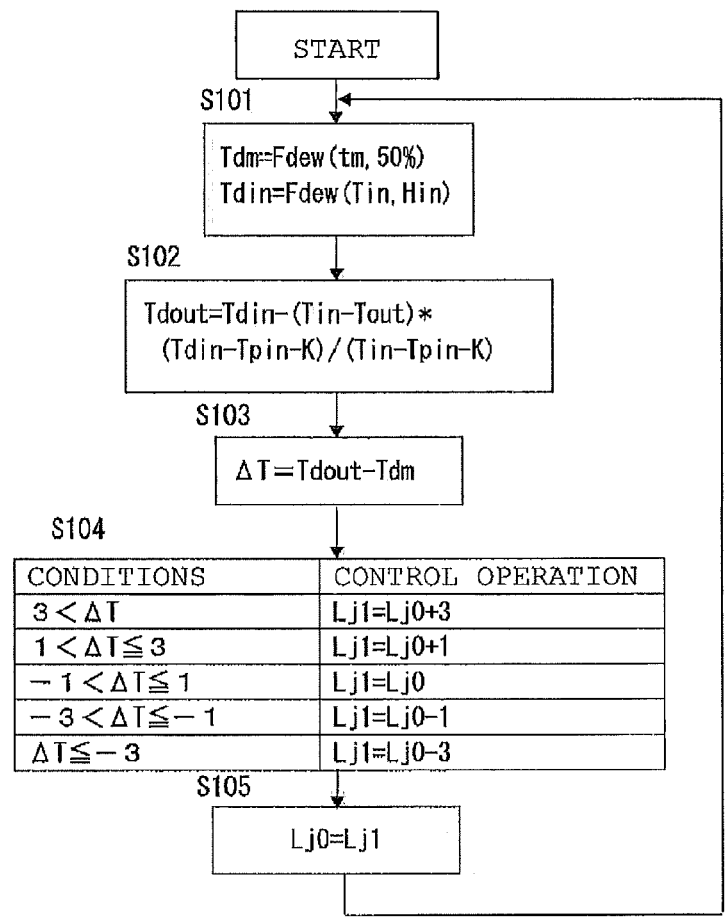
FIG. 3 is a table showing opening degree control operation of an adjustment valve according to $\Delta T$.
FIG. 4 is a flowchart illustrating the control operation processing flow of the opening degree of the adjustment valve.

FIG. 3 is a table showing opening degree control operation of the adjustment valve 9 according to $\Delta T$. Here, Lj1 denotes an opening degree (newly adjusted valve opening degree) of the adjustment valve 9 whose opening degree is newly adjusted. Lj0 denotes the opening degree (current adjustment valve opening degree) of the current adjustment valve 9. Under the condition when $\Delta T$ is larger than 3 ($3 < \Delta T$), Lj0 is added by 3 to be Lj1. (Lj1=Lj0+3) Under the condition when $\Delta T$ is larger than 1 and equal to or less than 3 ($1 < \Delta T \leq 3$), Lj0 is added by 1 to be Lj1. (Lj1=Lj0+1) Under the condition when $\Delta T$ is larger than −1 and equal to or less than 1 ($-1 < \Delta T \leq 1$), Lj0 is equal to Lj1. (Lj1=Lj0) Under the condition when $\Delta T$ is larger than −3 and equal to or less than −1 ($-3 < \Delta T \leq -1$) Lj0 is subtracted by 1 to be Lj1. (Lj1=Lj0−1) Under the condition when $\Delta T$ is equal to or less than −3 ($\Delta T \leq -3$), Lj0 is subtracted by 3 to be Lj1. (Lj1=Lj0−3)

FIG. 4 is a flowchart illustrating a control operation processing flow of the opening degree of the adjustment valve 9. Based on FIG. 4, the control operation processing flow of the adjustment valve 9 will be explained in detail. Firstly, the controller 4 calculates the target dew point temperature Tdm and the suction air dew point temperature Tdin. (step S101) These dew point temperatures are calculated based on a function Fdew (dry bulb temperature, relative humidity) that calculates a dew point temperature by inputting a dry bulb temperature and a relative humidity pre-mounted in a microcomputer. Next, the controller 4 simply calculates the outlet air dew point temperature Tdout. (step S102)

Figure 5:
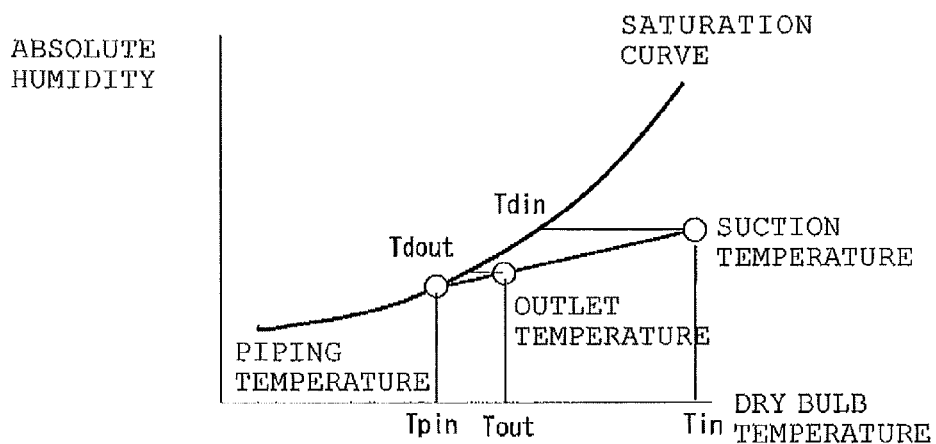
FIG. 5 is a psychrometric diagram.

In order to calculate the outlet air dew point temperature Tdout, the dew point temperature Tdin, the detected temperature Tout, and the detected temperature Tpin calculated by the detected dry bulb temperature Tin and the detected humidity Hin are used. (Refer to FIG. 2) As shown in FIG. 5, a temperature on a saturation curve on an extension of the suction air temperature and the outlet air temperature on the psychrometric diagram is specified as an evaporation temperature, then the evaporation temperature can be simply replaced for a evaporator inlet piping temperature Tpin+K. Here, K is a compensation coefficient obtained by the experiment. The controller 4 calculates the outlet air dew point temperature Tdout, then calculates a difference $\Delta T = Tdout - Tdm$ between the target dew point temperature Tdm and the outlet air dew point temperature Tdout. (step S103)

Then, the controller 4 changes the opening degree Lj1 of the adjustment valve 9 according to the calculated ΔT value. (step S104) The opening degree Lj1 of the adjustment valve 9 is changed based on the content of the above mentioned FIG. 3. That is, the opening degree Lj1 is determined by fluctuations of the current opening degree Lj0 of the adjustment valve 9. Thereafter, the controller 4 adjusts the opening degree of the adjustment valve 9 by making the determined opening degree Lj1 to be the current opening degree Lj0 of the adjustment valve 9. (step S105) The controller 4 repeats the operation to suitably adjust the opening degree of the adjustment valve 9.

As mentioned above, an air-conditioning apparatus according to Embodiment 1 can obtain a outlet dew point temperature without installing a humidity detector and a dew point temperature detector at the outlet side of the indoor unit 1, can be obtained and it is possible to control the outlet air dew point temperature Td to be the target dew point temperature Tdm, resulting in low-cost and high reliability. With the air-conditioning apparatus according to Embodiment 1, a outlet air relative humidity Hout can be calculated from the outlet air dew point temperature Td and the outlet air dry bulb temperature Tdout, so that when using a remote controller 8 capable of inputting humidity, the temperature and humidity of the outlet air 11 can be displayed, allowing user friendliness to be improved.

Embodiment 2

Figure 6:
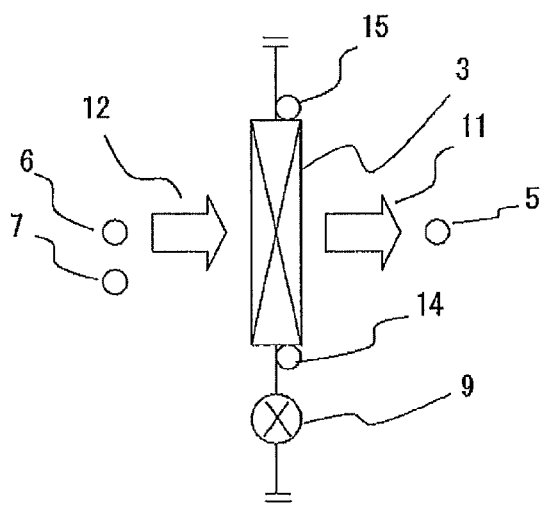
FIG. 6 is an illustrative drawing that illustrates the evaporator according to Embodiment 2 in detail.

FIG. 6 is an illustrative drawing that illustrates the evaporator 3 according to Embodiment 2 in detail. Based on FIG. 6, the evaporator 3 will be explained in detail along with a diagrammatic arrangement of the temperature detector related to the evaporator 3. Embodiment 2 is different from Embodiment 1 in that evaporator outlet piping temperature detector 5 is provided at the fluid outlet side of the evaporator 3. In addition, in Embodiment 2, descriptions will be given focusing on differences from Embodiment 1. The same signs will be given to the parts as Embodiment 1 and descriptions will be omitted.

The evaporator outlet piping temperature detector 15 detects a fluid temperature conducting in piping 10 at the outlet side of the evaporator 3. Here, the detection temperature by the evaporator outlet piping temperature detector 15 is defined as a detection temperature Tpout and used in the description below. Thereby, the detection temperature Tpout is transmitted to the controller 4 and used for the opening degree control of the adjustment valve 9. (Detailed descriptions will be given by a flowchart shown in FIG. 7) While the opening degree of the adjustment valve 9 is directly controlled according to a target temperature in Embodiment 1, it is controlled that a difference S between the evaporator inlet piping temperature Tpin and the evaporator outlet piping temperature Tpout is made to be a target value Sm in Embodiment 2. Embodiment 2 is the same as Embodiment 1 except the specification that the evaporator outlet piping temperature detector 15 is installed and its detection temperature Tpout is added.

Figure 7:
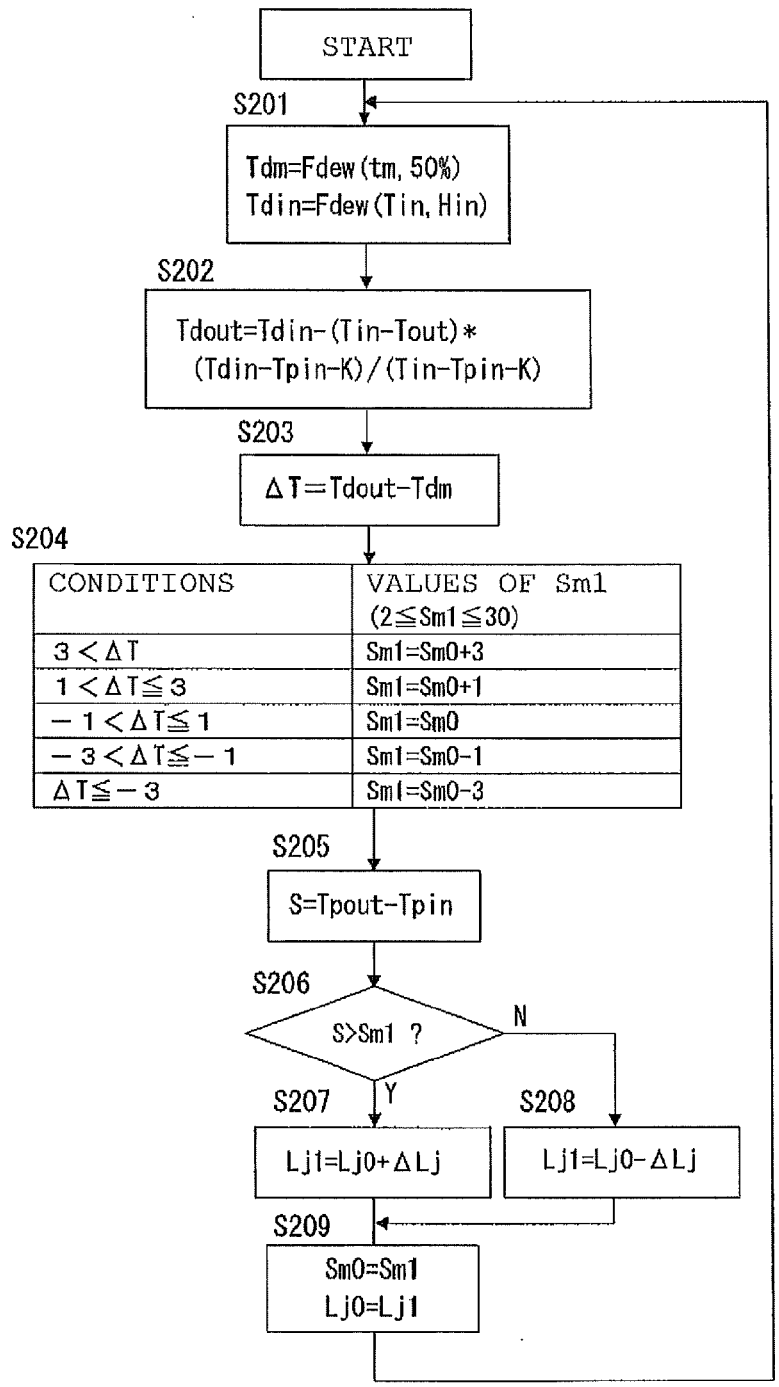
FIG. 7 is a flowchart illustrating a control operation processing flow of the opening degree of the adjustment valve.

FIG. 7 is a flowchart illustrating the control operation processing flow of the opening degree of the adjustment valve 9. Based on FIG. 7, the control operation processing flow of the adjustment valve 9 will be explained in detail. Firstly, the controller 4 calculates the target dew point temperature Tdm and the suction air dew point temperature Tdin like Embodiment 1. (step S201) These dew point temperatures are calculated based on a function Fdew (dry bulb temperature, relative humidity) that calculates a dew point temperature by inputting a dry bulb temperature and a relative humidity pre-mounted in a microcomputer. Next, the controller 4 simply calculates the outlet air dew point temperature Tdout. (step S202)

The controller 4 calculates the outlet air dew point temperature Tdout, then calculates a difference ΔT=Tdout−Tdm between the target dew point temperature Tdm and the outlet air dew point temperature Tdout. (step S203) Then, the controller 4 changes a target value Sm1 of the difference S between the evaporator outlet piping temperature Tpout and the evaporator inlet piping temperature Tpin according to the calculated value of the ΔT. (step S204) The target value 5 ml is adjusted by varying the target value Sm0. When the target value Sm1 exceeds an upper limit, the upper limit is fixed. When it becomes smaller than a lower limit, the lower limit is fixed. For example, in step S204, an example is shown in which the lower limit and the upper limits are set as 2 and 30, respectively.

Then, the controller 4 calculates a difference S between the evaporator outlet piping temperature Tpout and the evaporator inlet piping temperature Tpin. (step S205) Next, the controller 4 judges whether the difference S is larger than the target value S1. (step S206) After the controller 4 judges that the difference S is larger than the target value 31 (step S206: Y), a predetermined value ΔLj is added to Lj0 so that the difference S becomes equal to the target value 5 ml and the opening degree Lj1 of the adjustment valve 9 is changed so as to be opened by as much as ΔLj. (step S207)

On the other hand, when the controller 4 judges that the difference S is smaller than the target value S1 (step S206: N), a predetermined value ΔLj is subtracted from Lj0 so that the difference S becomes equal to the target value Sm1 and the opening degree Lj1 of the adjustment valve 9 is changed so as to be closed by as much as ΔLj. (step S208) Thereafter, the controller 4 adjusts the opening degree of the adjustment valve 9 by making the determined opening degree Lj1 to be the current opening degree Lj0 of the adjustment valve 9, and the target value Sm1 to be the current target value Sm0, respectively. (step 3209) The controller 4 repeats the operation to suitably adjust the opening degree of the adjustment valve 9.

As mentioned above, with an air-conditioning apparatus according to Embodiment 2, without installing a humidity detector and a dew point temperature detector at the outlet side of the indoor unit 1, an outlet dew point temperature can be obtained and it is possible to control the outlet air dew point temperature Td to be the target indoor dew point temperature Tdm, resulting in low-cost and high reliability. In the air-conditioning apparatus according to Embodiment 1, an outlet air relative humidity Hout can be calculated from the outlet air dew point temperature Td and the outlet air dry bulb temperature Tdout, so that when using a remote controller 8 capable of inputting humidity, the temperature and humidity of the outlet air 11 can be displayed, allowing user friendliness to be improved.

When directly controlling the opening degree of the adjustment valve 9 like Embodiment 1, a large opening degree of the adjustment valve 9 causes a large flow amount of the fluid flowing through the adjustment valve 9, resulting in leveling-off in evaporation ability because of poor heat exchange in the evaporator 3. When a refrigerant is used as the fluid, an unevaporated refrigerant returns to the heat source unit, that is liquid-back operation is started, reflecting a trend such that a burden on the compressor increases, and the refrigerant is centered on the heat source unit side to cause poor cooling ability. The trend can be avoided to some degree by setting an upper limit to the opening degree of the adjustment valve 9, however, a liquid-back trend cannot be avoided under some air conditions, or the like. A small upper limit of the adjustment valve 9 causes poor ability. Therefore, the opening degree control of the adjustment valve 9 by the difference S like Embodiment 2 enables the operation free from liquid-back by setting the lower limit to the target value Sm so that the difference S becomes equal to or larger than a predetermined value.

Embodiment 3

Figure 8:
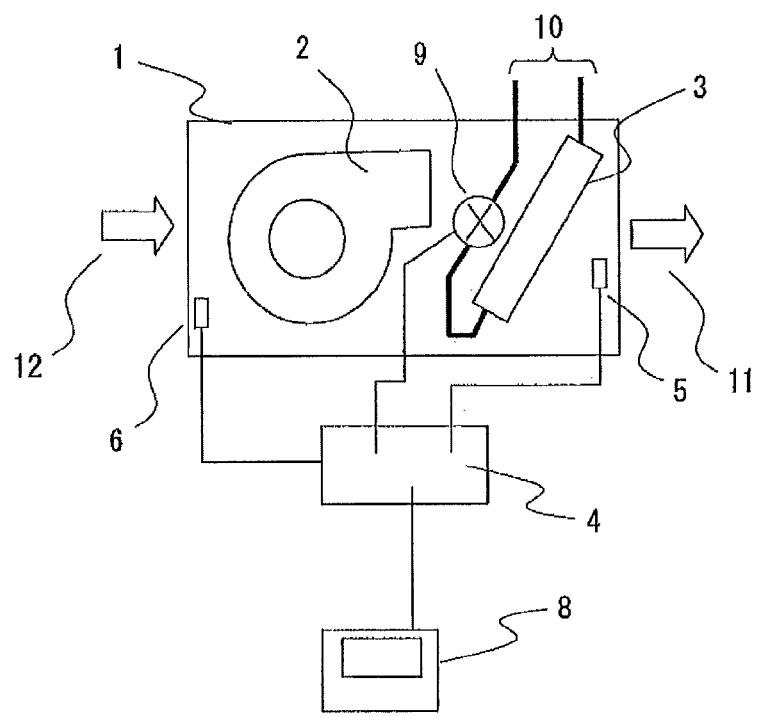
FIG. 8 is an internal configuration diagram illustrating a schematic internal configuration of the indoor unit of the air-conditioning apparatus according to Embodiment 3.

FIG. 8 is an internal configuration diagram illustrating the schematic internal configuration of the indoor unit 1 of the air-conditioning apparatus according to Embodiment 3. Based on FIG. 8, the internal configuration and operation of the indoor unit 1 will be explained. Embodiment 3 is different from Embodiment 1 in that without installing the suction air humidity detector 7, the outlet air dew point temperature Td is detected and the opening degree of the adjustment valve 9 is controlled. In Embodiment 3, descriptions will be given focusing on differences between Embodiments 1 and 2. The same signs will be given to the same parts as Embodiments 1 and 2, and descriptions will be omitted.

Figure 9:
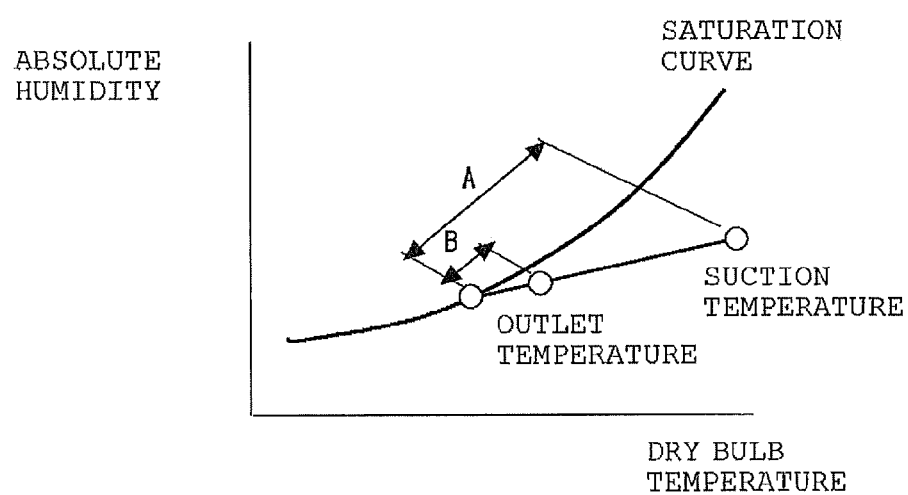
FIG. 9 is an illustrative drawing of a bypass factor BF.

A bypass factor BF shown in FIG. 9 is defined as BF=B/A. By selecting the evaporator 3 and an air volume so that BF becomes small, the difference between the outlet air dew point temperature Td and the outlet air dry bulb temperature Tout. At the time of Bf≤0.1, it is generally possible to treat that the outlet air dew point temperature Td=the outlet air dry bulb temperature Tout. (To be explained in detail in FIG. 14) That is, with the air-conditioning apparatus according to Embodiment 3, it is possible to detect the outlet air dew point temperature Td from the outlet air dry bulb temperature Tout without installing the suction air humidity detector 7.

Figure 10:
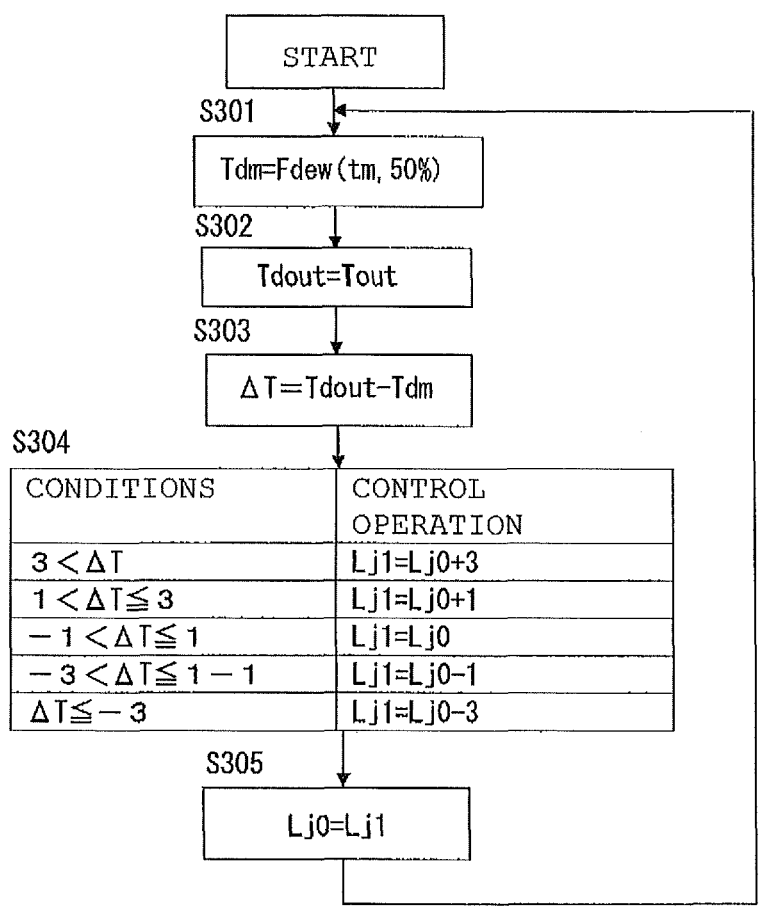
FIG. 10 is a flowchart illustrating the control operation processing flow of the opening degree of the adjustment valve.

FIG. 10 is a flowchart illustrating the control operation processing flow of the opening degree of the adjustment valve 9. Based on FIG. 10, the control operation processing flow of the adjustment valve 9 will be explained in detail. In addition, the definition of Tdout is changed compared with FIG. 4, descriptions being omitted. Step 304 may be changed like FIG. 7 in the same way, descriptions being omitted. Firstly, the controller 4 calculates a target dew point temperature Tdm. (step S301) The dew point temperature is calculated based on a function Fdew that calculates a dew point temperature by inputting a dry bulb temperature and relative humidity pre-mounted in a microcomputer. Next, the controller 4 simply calculates the outlet air dew point temperature Tdout. (step S302)

The outlet air dew point temperature Tdout is calculated using the detected temperature Tout. (Refer to FIG. 9) The controller 4 calculates the outlet air dew point temperature Tdout, then calculates a difference ΔT=Tdout−Tdm between the target dew point temperature Tdm and the outlet air dew point temperature Tdout. (step S303) Then, the controller 4 changes the opening degree Lj1 of the adjustment valve 9 according to the calculated ΔT value. (step S304) The opening degree Lj1 of the adjustment valve 9 is changed based on the content of the above mentioned FIG. 3. Thereafter, the controller 4 adjusts the opening degree of the adjustment valve 9 by making the determined opening degree Lj1 to be the current opening degree Lj0 of the adjustment valve 9. (step S305) The controller 4 repeats the operation to suitably adjust the opening degree of the adjustment valve 9.

Figure 14:
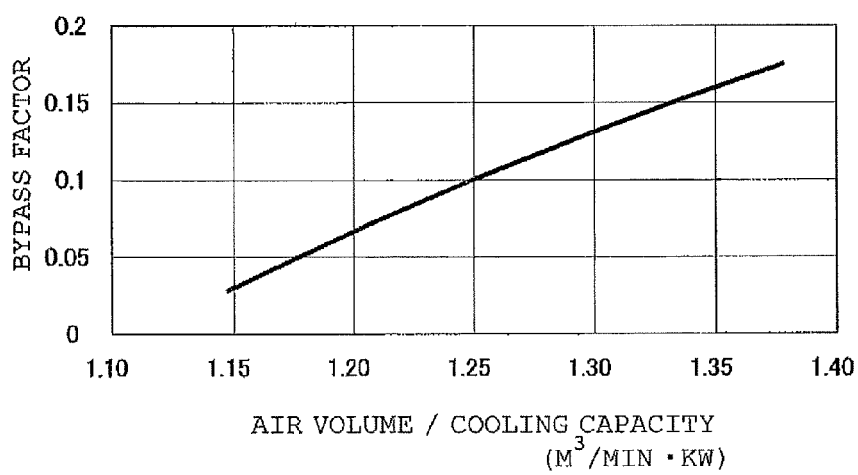
FIG. 14 is a graph illustrating the tendency of the bypass factor BF.

FIG. 14 is a graph illustrating the tendency of the bypass factor BF. The trend of the bypass factor BF will be explained based on FIG. 14. In FIG. 14, the vertical axis denotes the bypass factor BF, and the horizontal axis denotes air volume/cooling ability (m³/min kW), respectively. The bypass factor BF is determined mainly by the specification (size, fin pitch, etc.) of the evaporator 3 and air volume. By determining the specification of the evaporator 3 under predetermined conditions so that the cooling ability reaches a predetermined target value, the cooling ability and the air volume play a dominant role in deciding the bypass factor BF.

Therefore, the bypass factor BF can be roughly determined by making the air volume/cooling ability (m³/min kW) an index. For example, according to characteristics of the bypass factor BF shown in FIG. 14, the air volume and the cooling ability are specified so as to make the air volume/cooling ability to be equal to or less than 1.25, a heat exchanger satisfying the conditions is designed, and it is used as the evaporator 3. Then, an air-conditioning apparatus achieving the bypass factor BF≤0.1 can be configured. Incidentally, when the opening degree of the adjustment valve 9 is small, the flow amount of the fluid becomes small, so that the fluid temperature flowing through the evaporator 3 is strongly subjected to the suction air temperature, reflecting a trend that the temperature difference between the inlet and outlet becomes large.

Figure 11:
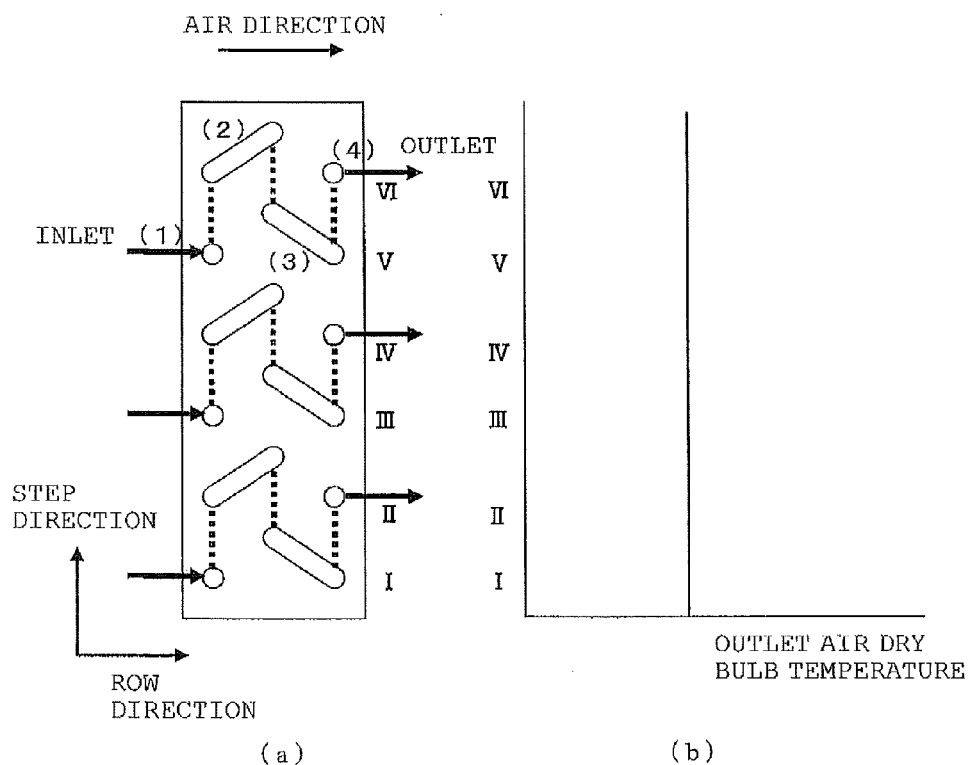
FIG. 11 is an illustrative drawing that illustrates an example of piping penetrating through the evaporator.
Figure 12:
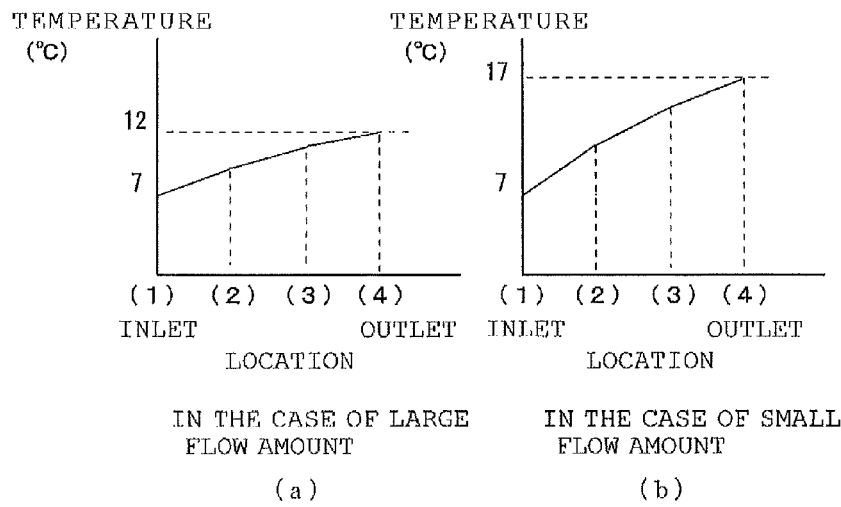
FIG. 12 is an illustrative drawing that illustrates temperature characteristics of the fluid in the evaporator.

FIG. 11 is an illustrative drawing that illustrates an example of piping penetrating through the evaporator 3. FIG. 12 is an illustrative drawing that illustrates temperature characteristics of a fluid in the evaporator 3. Based on FIGS. 11 and 12, descriptions will be given to a suitable piping arrangement as the evaporator 3. FIG. 11(*a*) is a longitudinal sectional view showing a schematic sectional configuration of the evaporator 3. FIG. 11(*b*) is a graph showing a temperature distribution of the outlet air 11 blown out from the evaporator 3. Correspondence relations of FIGS. 11(*a*) and 11(*b*) are shown by I to VI. FIGS. 12(*a*) and 12(*b*) show temperature characteristics when the flow amount being large and small, respectively. In FIG. 12, the vertical axis denotes the temperature [° C.], the horizontal axis denoting the location.

The fluid in the evaporator 3 flows in the order (1)-(2)-(3)-(4) as shown in FIG. 11(*a*). FIG. 12 shows a tendency of each temperature. When the flow amount of the fluid is small, the temperature difference between the inlet and the outlet becomes large as shown in FIG. 12(*b*). As shown in FIG. 11, in piping arrangement of the evaporator 3, arrangement of two steps or less in the same row in a pass is common so that no lack of uniformity in the temperature occurs in a step direction (an upward arrow shown in the figure). Accordingly, in the evaporator 3 according to Embodiment 3, to adopt arrangement of two steps in the same row is desirable. In FIG. 11, an example is given to a case in which the number of the row (right-pointing arrows in the figure) is three, however, one or two steps are arranged in the same row even when the number of the row is different.

Figure 13:
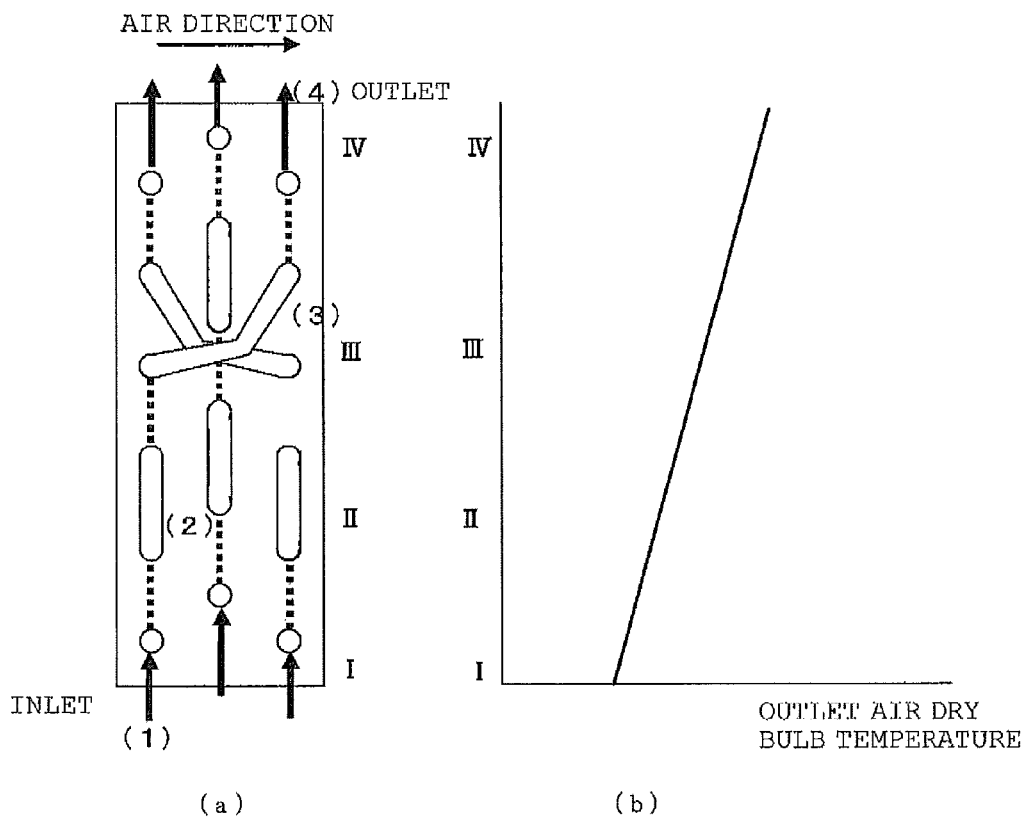
FIG. 13 is an illustrative drawing that illustrates another example of piping penetrating through the evaporator.

FIG. 13 is an illustrative drawing that illustrates another example of piping penetrating into the evaporator 3. Based on FIG. 13, piping arrangement that is not suitable as the evaporator 3 will be explained. FIG. 13(*a*) is a longitudinal sectional view showing a schematic sectional configuration of the evaporator 3. FIG. 13(*b*) is a graph showing a temperature distribution of the outlet air 11 blown out from the evaporator 3. Correspondence relations of FIGS. 13(*a*) and 13(*b*) are shown by I to VI. As shown in FIG. 13, when many steps are arranged in the same row in a single pass, lack of uniformity in the outlet air temperature occurs in a step direction. When the flow amount of the fluid decreases, lack of uniformity in the temperature tends to increase. When lack of uniformity in temperature of the outlet air 11 becomes large, the bypass factor of the evaporator 3 becomes large such that a location where the temperature of the piping 10 becomes equal to or larger than the dew point and a location where the temperature becomes equal to or less than the dew point. Therefore, it is desirable not to select a heat exchanger having such a pass arrangement.

As mentioned above, with an air-conditioning apparatus according to Embodiment 3, without installing a humidity detector and a dew point temperature detector at the outlet side of the indoor unit 1, and without installing the humidity detector at the inlet of the indoor unit 1, an outlet dew point temperature can be obtained, thereby achieving low-cost and high reliability. A piping arrangement, in which, in a single pass of the evaporator 3 described in Embodiment 3, two stages or less are arranged in the same row, can be used for Embodiment 1 or 2. When using such the evaporator 3 for Embodiment 1 or 2, the outlet air dew point temperature can be calculated with high precision.

Embodiment 4

FIG. 15 is a circuit configuration diagram showing a schematic circuit configuration of the air-conditioning apparatus according to Embodiment 4 of the present invention. Based on FIG. 15, operation of the air-conditioning apparatus 100, especially differences among Embodiments 1 to 3 will be explained. Embodiment 4 is different from Embodiments 1 to 3 in that the outlet dew point temperature is controlled by the capacity control of the heat source unit 200. In Embodiment 4, descriptions will be mainly given focusing on differences among Embodiments 1 to 3. The same signs will be given to the parts as Embodiments 1 to 3 and descriptions will be omitted. In Embodiment 4, the case in which the air-conditioning apparatus 100 performs cooling operation will be explained.

The air-conditioning apparatus 100 according to Embodiment 4 is largely composed of the indoor unit 21 and the heat source unit 20. In the indoor unit 21, the throttle device 25 (corresponding to the adjustment valve 9), the indoor unit side heat exchanger 26 (corresponding to the evaporator 3), the indoor unit side blower 28 (corresponding to the blower 2), outlet air temperature detector 35 (corresponding to the outlet air temperature detector 5), the suction air temperature detector 33 (corresponding to the suction air temperature detector 6), the suction air humidity detector 34 (corresponding to the suction air humidity detector 7), the liquid-side piping temperature detector 31 (corresponding to the evaporator inlet fluid temperature detector 14), the gas-side piping temperature detector 32 (corresponding to the evaporator outlet piping temperature detector 15), and the indoor unit side controller 37 (corresponding to the controller 4) are mainly mounted.

In the heat source unit 20, the compressor 22, the four-way valve 23, the heat source side heat exchanger 24, the heat source side blower 27, the high-pressure pressure detector 29, the low-pressure pressure detector 30, and heat source unit side controller 36 are mainly mounted. In the air-conditioning apparatus 100, the compressor 22, the four-way valve 23, the heat source side heat exchanger 24, the throttle device 25, and the indoor unit side heat exchanger 26 are serially connected in order by piping to form a refrigerant circuit. The air-conditioning apparatus 100 can execute the heating or the cooling operation by switching the four-way valve 23 to reverse the refrigerant flow.

Descriptions will be given to functions of each above-mentioned equipment (each equipment mounted in the heat source unit 20). The heat source unit 20 is installed outdoors and the compressor 22, the four-way valve 23, the heat source side heat exchanger 24, and the heat source side blower 27 are mounted as mentioned above. The compressor 22 sucks the refrigerant to compress and turn it into a high-temperature high-pressure state. It may be composed by such as a capacity-controllable inverter compressor. The four-way valve 23 functions as a flow pass switching device that switches the refrigerant flow. The heat source side heat exchanger 24 performs heat exchange between the air supplied from the heat source side blower 27 installed in the vicinity and the refrigerant conducting through piping 10 to condense and liquefy or evaporate and gasify the refrigerant. The heat source side blower 27 has a function to supply the air taken from outside to the heat source side heat exchanger 24.

In the heat source unit 20, the high-pressure pressure detector 29, the low-pressure pressure detector 30, and the heat source unit side controller 36 are mounted as mentioned above. The high-pressure pressure detector 29 is installed in the outlet side piping of the compressor 22 to detect the (high) pressure of the refrigerant discharged from the compressor 22. The low-pressure pressure detector 30 is installed in the suction side piping of the compressor 22 to detect the (low) pressure of the refrigerant sucked by the compressor 22. The heat source unit side controller 36 receives pressure information detected by the high-pressure pressure detector 29 and the low-pressure pressure detector 30 to control the drive frequency of the compressor 22, the switching of the four-way valve 23, and the rotation speed of the heat source side blower 27. The heat source unit side controller 36 can perform transmission and reception with the indoor unit side controller 37.

Here, the refrigerant flow at the time of the cooling operation of the air-conditioning apparatus 100 will be explained. When the air-conditioning apparatus 100 starts the cooling operation, the compressor 22 is driven at first. The high-temperature high-pressure gas refrigerant discharged from the compressor 22 flows into the heat source side heat exchanger 24 via the four-way valve 23. In the heat source side heat exchanger 24, the gas refrigerant is condensed and liquefied to turn into the low-temperature high-pressure liquid refrigerant while dissipating heat into the air. The liquid refrigerant flows out from the heat source side heat exchanger 24 into the indoor unit 21. The refrigerant flown into the indoor unit 21 is decompressed by the throttle device 25 to flow into the indoor unit side heat exchanger 26.

The refrigerant flown into the indoor unit side heat exchanger 26 is evaporated and gasified through the heat exchange with the air. That is, thereby, the refrigerant cools the air by absorbing heat from the air in the indoor unit side heat exchanger 26 to perform the cooling operation by blowing out the cooled air into an air-conditioning subject area. The refrigerant flows out from the indoor unit 21 to be absorbed again by the compressor 22 via the four-way valve 23. As mentioned above, the refrigerant circulates in the air-conditioning apparatus 100 at the time of the cooling operation.

Next, descriptions will be given to the air flow at the time of the cooling operation of the air-conditioning apparatus 100. When the air-conditioning apparatus 100 starts the cooling operation, the indoor unit side blower 28 is driven in the indoor unit 21. High-temperature high-humidity air flows into the indoor unit side heat exchanger 26 by the indoor unit side blower and performs heat exchange with the low-temperature refrigerant in the indoor unit side heat exchanger 26. After being partly dehumidified, it turns into low-temperature air to be blown out from the indoor unit 21. (outlet air 38 (corresponding to outlet air 11))

At the inlet side of the indoor unit side heat exchanger 26, the suction air temperature detector 33 and suction air humidity detector 34 are installed, while at the outlet side, the outlet air temperature detector 35 is installed. Information on air temperature and humidity information detected by each is transmitted to the indoor unit side controller 37. The indoor unit side controller 37 received the information communicates with the heat source unit side controller 36 based on the information. Then, the heat source unit side controller 36 controls the capacity of the compressor 22 based on information transmitted from the indoor unit side controller 37.

Figure 16:
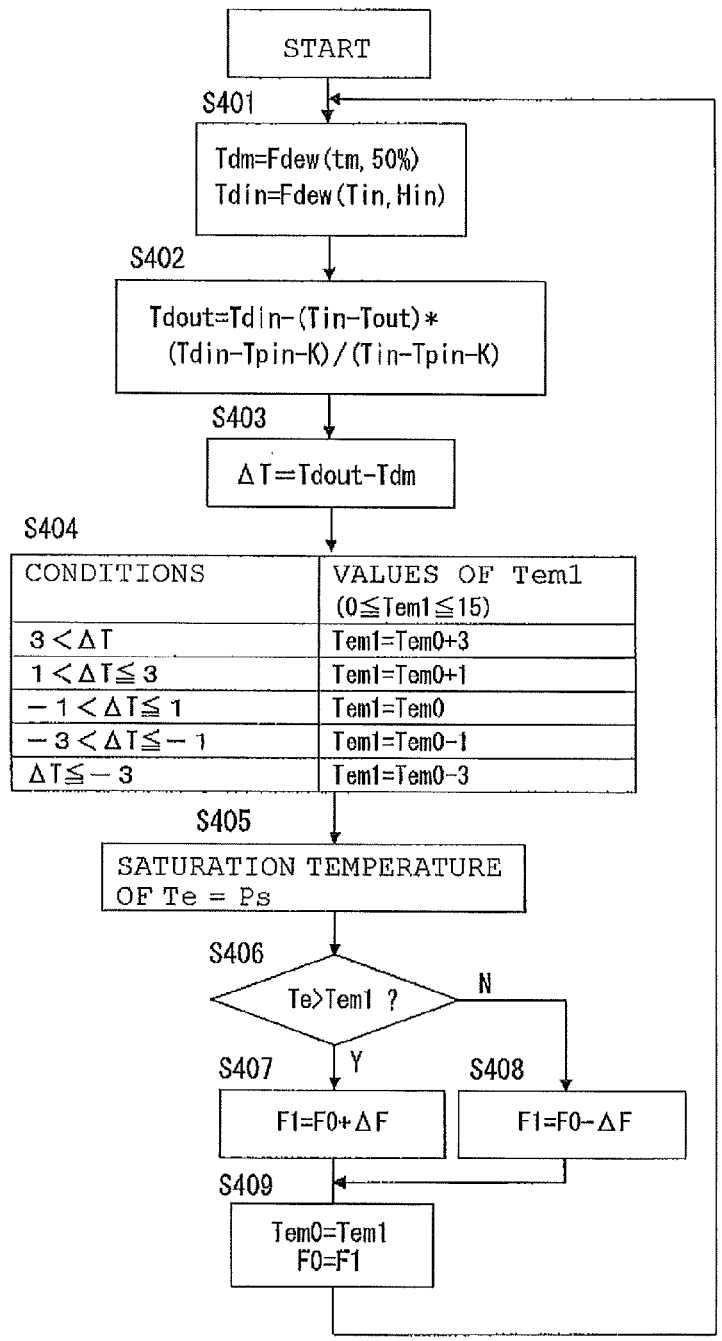
FIG. 16 is a flowchart showing an example of the capacity control processing flow of a compressor.

FIG. 16 is a flowchart showing an example of the capacity control processing flow of the compressor 22. Based on FIG. 16, an example of the capacity control processing flow of the compressor 22 will be explained. Firstly, the indoor unit side controller 37 (or the heat source unit side controller 36) calculates the target dew point temperature Tdm and the suction air dew point temperature Tdin like Embodiment 2. (step S401) These dew point temperatures are calculated based on a function Fdew (dry bulb temperature, relative humidity) that calculates a dew point temperature by inputting a dry bulb temperature and relative humidity pre-mounted in a microcomputer. Next, the indoor unit side controller 37 simply calculates the outlet air dew point temperature Tdout. (step S402)

The indoor unit side controller 37 calculates the outlet air dew point temperature Tdout, then calculates a difference $\Delta T=Tdout-Tdm$ between the target dew point temperature Tdm and the outlet air dew point temperature Tdout. (step S403) Then, the indoor unit side controller 37 changes a target value Tem1 of the heat source unit evaporation temperature Te according to the calculated $\Delta T$ value. (step S404) The target value Tem1 is adjusted by varying the current target value Tem0. When the target value Tem1 exceeds an upper limit, the upper limit is fixed. When it becomes smaller than a lower limit, the lower limit is fixed. For example, in step S404, an example is shown in which the lower limit and the upper limits are set as 15 and 0, respectively. In addition, steps S401 to S404 may be performed by the heat source unit side controller 36.

After changing the heat source unit evaporation temperature Te into the target value Tem1, the heat source unit side controller 36 calculates the heat source unit evaporation temperature Te by calculating the saturation temperature of the pressure detected by the low-pressure pressure detector 30. (step S405) Then, the heat source unit side controller 36 judges whether the heat source unit evaporation temperature Te is larger than the target value Tem1. (step S406) When the heat source unit side controller 36 judges that the heat source unit evaporation temperature Te is larger than the target value Tem1, (step S406: Y) a predetermined value $\Delta F$ is added to F0 so that the heat source unit evaporation temperature Te is equal to the target value Tem1 to increase the frequency F1 of the compressor 22 by $\Delta F$. (step S407)

To the contrary, when the heat source unit side controller 36 judges that the heat source unit evaporation temperature Te is smaller than the target value Tem1 (step S406: N), a predetermined value $\Delta F$ is subtracted from F0 so that the heat source unit evaporation temperature Te is equal to the target value Tem1 to decrease the frequency F1 of the compressor 22 by $\Delta F$. (step S408) Thereafter, the heat source unit side controller 36 adjusts the frequency of the compressor 22 by setting the determined frequency F1 as the current frequency F0 of the compressor 22 and the target value Tem1 as the current target value Tem0, respectively. (step S409) The heat source unit side controller 36 repeats the operation to suitably adjust the frequency of the compressor 22.

Figure 17:
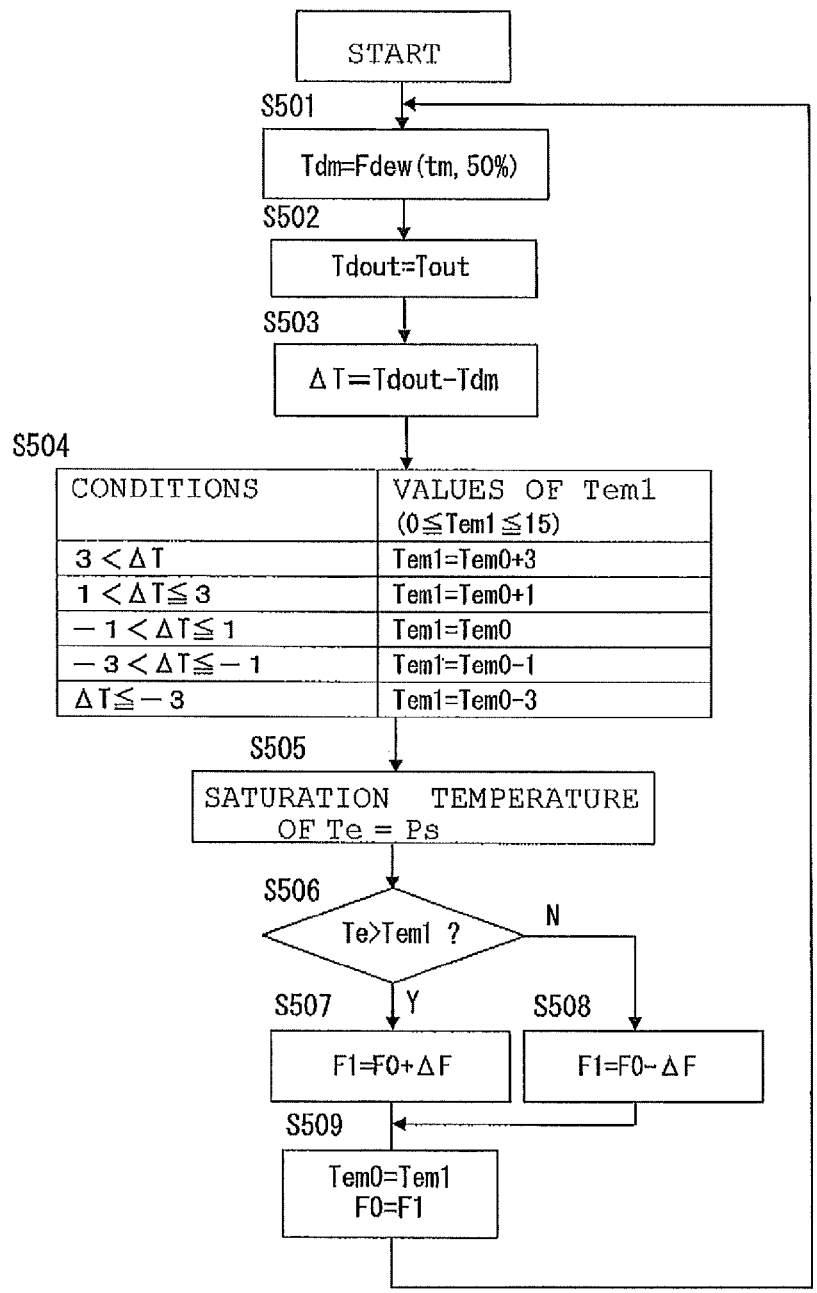
FIG. 17 is a flowchart showing another example of the capacity control processing flow of the compressor.

FIG. 17 is a flowchart showing another example of the capacity control processing flow of the compressor 22. Based on FIG. 17, an example of the capacity control processing flow of the compressor 22 will be explained. In FIG. 16, the capacity control processing flow of the compressor 22 is shown when adopting a method for calculating the outlet air dew point temperature Tdout of Embodiments 1 and 2. In FIG. 17, the capacity control processing flow of the compressor 22 is shown when adopting a method for calculating the outlet air dew point temperature Tdout of Embodiment 3.

Firstly, the indoor unit side controller 37 (or the heat source unit side controller 36) calculates the target dew point temperature Tdm. (step S501) The dew point temperature is calculated based on a function Fdew that calculates a dew point temperature by inputting a dry bulb temperature and relative humidity pre-mounted in a microcomputer. Next, the indoor unit side controller 37 simply calculates the outlet air dew point temperature Tdout. (step S502) The outlet air dew point temperature Tdout is calculated using the detected temperature Tout. The indoor unit side controller 37 calculates the outlet air dew point temperature Tdout, then calculates a difference $\Delta T=Tdout-Tdm$ between the target dew point temperature Tdm and the outlet air dew point temperature Tdout. (step S503)

Then, the indoor unit side controller 37 changes a target value Tem1 of the heat source unit evaporation temperature Te according to the calculated $\Delta T$ value. (step S504) The target value Tem1 is adjusted by varying the current target value Tem0. When the target value Tem1 exceeds an upper limit, the upper limit is fixed. When it becomes smaller than a lower limit, the lower limit is fixed. For example, in step S504, an example is shown in which the lower limit and the upper limits are set as 15 and 0, respectively. In addition, steps S501 to S504 may be performed by the heat source unit side controller 36.

After changing the heat source unit evaporation temperature Te into the target value Tem1, the heat source unit side controller 36 calculates the heat source unit evaporation temperature Te by calculating the saturation temperature of the pressure detected by the low-pressure pressure detector 30. (step S505) Then, the heat source unit side controller 36 judges whether the heat source unit evaporation temperature Te is larger than the target value Tem1. (step S506) When the heat source unit side controller 36 judges that the heat source unit evaporation temperature Te is larger than the target value Tem1, (step S506: Y) a predetermined value $\Delta F$ is added to F0 so that the heat source unit evaporation temperature Te is equal to the target value Tem1 to increase the frequency F1 of the compressor 22 by $\Delta F$. (step S507)

To the contrary, when the heat source unit side controller 36 judges that the heat source unit evaporation temperature Te is smaller than the target value Tem1 (step 3506: N), a predetermined value $\Delta F$ is subtracted from F0 so that the heat source unit evaporation temperature Te is equal to the target value Tem1 to decrease the frequency F1 of the compressor 22 by $\Delta F$. (step S508) Thereafter, the heat source unit side controller 36 adjusts the frequency of the compressor 22 by setting the determined frequency F1 as the current frequency F0 of the compressor 22 and the target value Tem1 as the current target value Tem0, respectively. (step S509) The heat source side controller 36 repeats the operation to suitably adjust the frequency of the compressor 22. Thus, the same effect as FIG. 16 can be obtained by the capacity control of the compressor 22.

Figure 18:
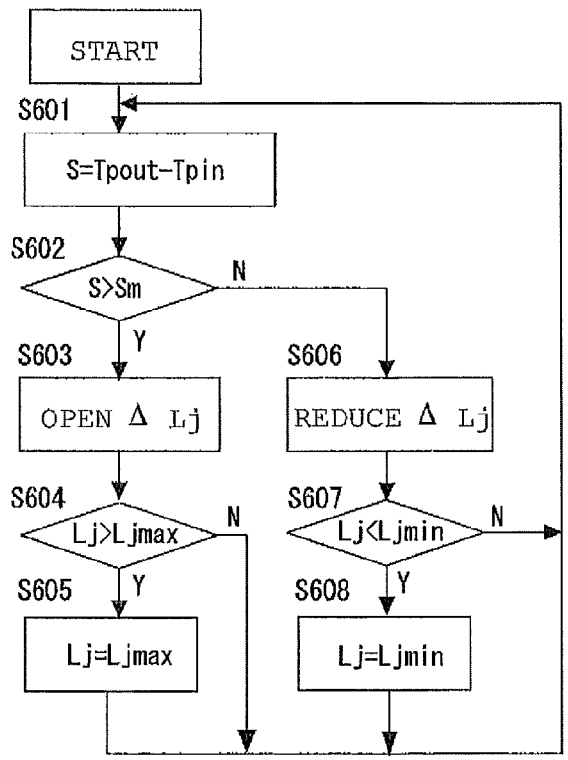
FIG. 18 is a flowchart showing a control operation flow of the throttle device of the indoor unit.

FIG. 18 is a flowchart showing the control operation flow of the throttle device of the indoor unit 21. Based on FIG. 18, processing flow of controlling the opening degree of the throttle device 25 of the indoor unit 21 will be explained in detail. Firstly, the indoor unit side controller 37 calculates a difference S=Tpout−Tpin between the detected temperature Tpin of the liquid-side piping temperature detector 31 and the detected temperature Tpout of the gas-side piping temperature detector 32. (step S601) Then, the indoor unit side controller 37 compares the difference S with the target value Sm to judge whether to open the throttle device 25. (step S602)

When a judgment result is S>Sm (step S602:Y), the indoor unit side controller 37 controls the throttle device 25 to be opened by ΔLj. (step S603) Thereby, the indoor unit side controller 37 judges whether the opening degree Lj of the throttle device 25 exceeds the maximum opening degree Ljmax. (step S604) When the judgment result exceeds the maximum opening degree Ljmax (step S604: Y), the indoor unit side controller 37 limits the opening degree Lj of the throttle device 25 to be the maximum opening degree Ljmax (step S605).

On the other hand, when the judgment result is S<Sm (step S602: N), the indoor unit side controller 37 controls the throttle device 25 to be closed by ΔLj. (step S606) Thereby, the indoor unit side controller 37 judges whether an opening degree Lj of the throttle device 25 is less than the minimum opening degree Ljmin. (step S607) When the judgment result is less than the minimum opening degree Ljmin (step S607: Y), the indoor unit side controller 37 limits the opening degree Lj of the throttle device 25 to be the minimum opening degree Ljmin (step S608). A preset predetermined value is used for the target value Sm.

As mentioned above, an air-conditioning apparatus 100 according to Embodiment 4, without installing a humidity detector and a dew point temperature detector at the outlet side of the indoor unit 21, an outlet dew point temperature can be obtained and it is possible to control the outlet air dew point temperature Td to be the target indoor dew point temperature Tdm, resulting in low-cost and high reliability. With the air-conditioning apparatus 100 according to Embodiment 4, an outlet air relative humidity Hout can be calculated from the outlet air dew point temperature Td and the outlet air dry bulb temperature Tdout, so that when using a remote controller capable of inputting humidity, the temperature and humidity of the outlet air 38 can be displayed, allowing user friendliness to be improved.

Embodiment 5

Figure 19:
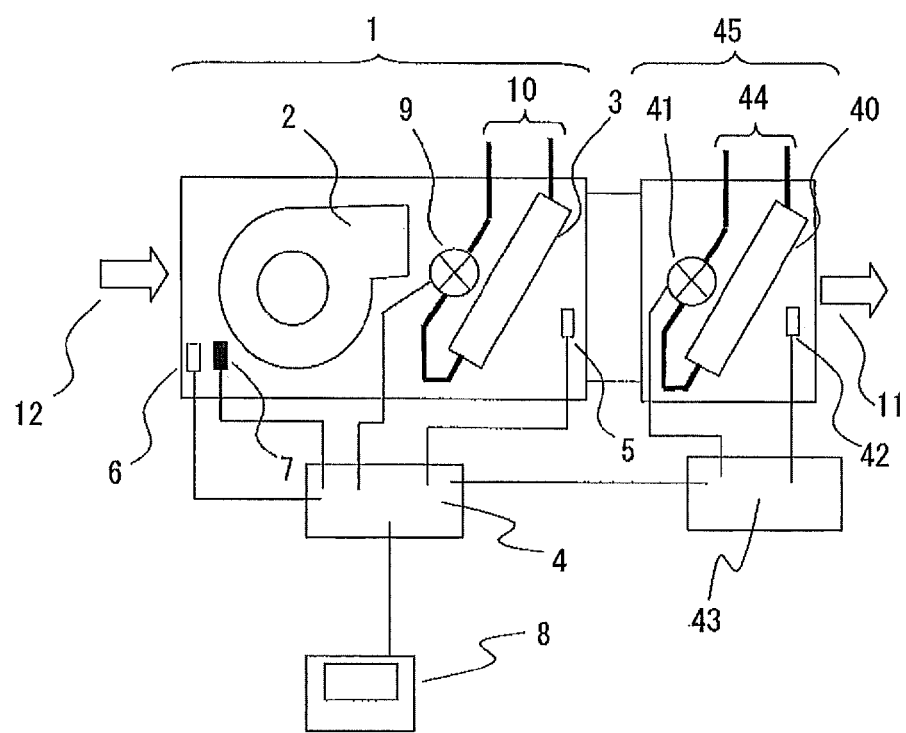
FIG. 19 is an internal configuration diagram illustrating a schematic internal configuration of the indoor unit of the air-conditioning apparatus and the reheat unit according to Embodiment 5.

FIG. 19 is an internal configuration diagram illustrating a schematic internal configuration of an indoor unit 1 and a reheat unit 45 of the air-conditioning apparatus according to Embodiment 5. Based on FIG. 19, descriptions will be given to the internal configuration and operation of the indoor unit 1 and the reheat unit 45, especially different points from Embodiments 1 to 4. Embodiment 5 is different from Embodiments 1 to 4 in that the reheat unit 45 is connected. In Embodiment 5, descriptions will be mainly given focusing on differences among Embodiments 1 to 4. The same signs will be given to the same parts as Embodiments 1 to 4, and descriptions will be omitted.

The reheat unit 45 is installed at the outlet side of the indoor unit 1 explained, for example, in Embodiment 1. In the reheat unit 45, as shown in FIG. 19, the condenser 40, the adjustment valve 41, and the outlet air temperature detector are built-in. The condenser 40 is connected with the adjustment valve 41, being connected with a heat source unit (not shown) via piping 44. The outlet air temperature detector 42 detects the outlet air temperature Trout of the reheat unit 45 to transmit the information to the controller 43. The controller 43 control the opening degree of the adjustment valve 41 based on the outlet air temperature Trout. The controller 43 can transmit/receive signals to/from the controller 44.

The low-temperature outlet air 11 whose dew point temperature is controlled by the indoor unit 1 is humidified by passing through the condenser 40 in the reheat unit 45. In the outlet side of the condenser 40, the outlet air temperature detector 42 is installed and the outlet air temperature Trout of the reheat unit 45 is detected. From the remote controller 8, a target indoor dry bulb temperature Tm is set. The controller 4 controls the adjustment valve 41 so that the outlet air temperature Trout detected by the outlet air temperature detector 42 becomes the Tm.

As explained in Embodiment 1, the heat source unit may be any of for dedicated cooling operation, for cooling-heating switching operation, a multi-type in which a plurality of indoor units are connected, and cooling-heating simultaneously operable type, so that operation form is not limited in particular. That is, the evaporator 3 and the condenser 40 may be connected with the same refrigerant system, and the evaporator 3 and the condenser 40 may be connected with a separate refrigerant system. Further, an electric heater may be used in which a controller is installed so as to be able to control the capacity. Functions are the same even if the reheat unit 45 is built-in in the indoor unit 1.

Figure 20:
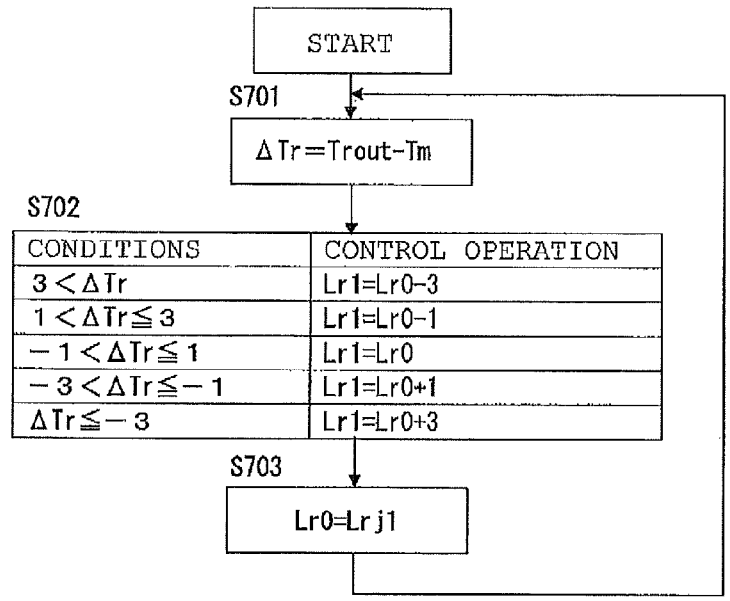
FIG. 20 is a flowchart illustrating a control operation processing flow of the opening degree of the adjustment valve in detail.
Figure 21:
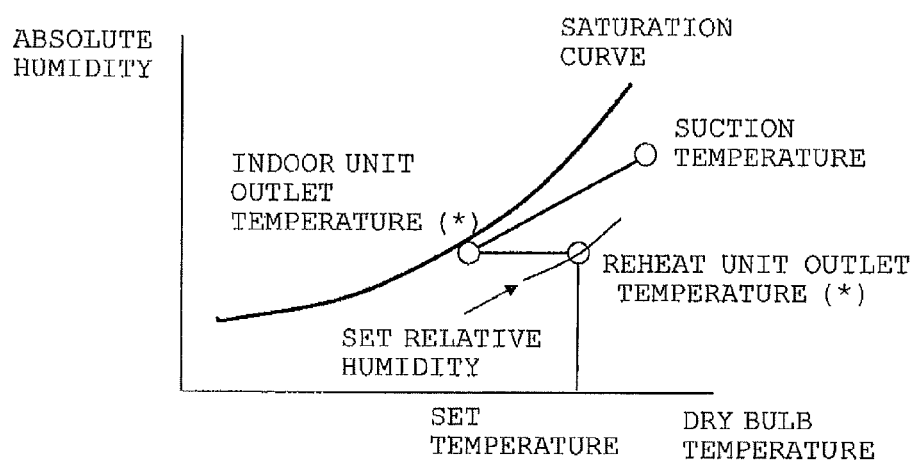
FIG. 21 is a graph showing the relation between temperature and humidity of the outlet air of the reheat unit.

FIG. 20 is a flowchart illustrating a control operation processing flow of the opening degree of the adjustment valve 41. FIG. 21 is a graph showing a relation between temperature and humidity of the outlet air of the reheat unit 45. Based on FIGS. 20 and 21, processing flow of controlling the opening degree of the adjustment valve 41 will be explained in detail. Firstly, the controller 43 calculates a difference ΔTr between the outlet air temperature Trout and the target indoor dry bulb temperature Tm. (step S701) Then, the controller 43 changes the opening degree Lr1 of the adjustment valve 41 according to the calculated difference ΔTr. (step S702) The opening degree Lr1 of the adjustment valve 41 is adjusted by variations from the current opening degree Lr0 of the adjustment valve 41. (step S703) The controller 43 repeats the operation to suitably adjust the opening degree of the adjustment valve 41.

As mentioned above, an air-conditioning apparatus according to Embodiment 5, without installing a humidity detector and a dew point temperature detector at the outlet side of the indoor unit 1, an outlet dew point temperature can be obtained and it is possible to control the outlet air temperature Trout to be the target indoor dry bulb temperature Tm, resulting in low-cost and high reliability. Since the outlet air 11 of the indoor unit 1 is, as explained in Embodiments 1 and 2, controlled to be the dew point temperature target value Tdm, the condenser 40 undergoes only a sensible heat exchange, no input/output of humidity, and the dew point temperature of the reheat outlet air also becomes the dew point temperature target value Tdm.

As mentioned above, since the dew point temperature becomes Tdm and the dry bulb temperature becomes Tm, and the outlet air 11 of the reheat unit 45 becomes the target temperature, as shown in FIG. 21, the temperature and the humidity of the outlet air 11 of the reheat unit 45 becomes the values equal to those set by the remote controller 8. In Embodiment 5, descriptions are given with an example in which the controller 43 controls the opening degree of the adjustment valve 41, the controller 4 may control the opening degree of the adjustment valve 41. In addition, the controller 4 may be made to be in charge of the functions of the controller 43.

The invention claimed is:

1. An indoor unit comprising:
an evaporator,
a blower that supplies air to the evaporator,
a suction air temperature detector that detects a suction air temperature in the upstream of the air flow of the evaporator,
an outlet air temperature detector that detects the outlet air temperature in the downstream of the air flow of the evaporator,
an evaporator inlet fluid temperature detector that detects the fluid temperature in the fluid inlet side of the evaporator,
an adjustment valve that adjusts the flow amount of the fluid made to be flowed into the evaporator, and
a controller that calculates a suction air dew point temperature from suction air temperature information detected by the suction air temperature detector to calculate an outlet air dew point temperature based on the suction air dew point temperature, the suction air temperature, the outlet air temperature, and the evaporator inlet piping temperature.

2. The indoor unit of claim 1 comprising:
a suction air humidity detector that detects suction air humidity at the upstream side of the air flow in the evaporator, wherein
the controller calculates a suction air dew point temperature from suction air temperature information detected by the suction air temperature detector and suction humidity information detected by the suction air humidity detector to calculate an outlet air dew point temperature based on the suction air dew point temperature, the suction air temperature, the outlet air temperature, and the evaporator inlet piping temperature.

3. The indoor unit of claim 2, wherein
the controller controls the opening degree of the adjustment valve so that the calculated outlet dew point temperature reaches a predetermined target value.

4. The indoor unit of claim 2, wherein
an evaporator outlet piping temperature detector that detects a fluid temperature at the fluid outlet side of the evaporator is provided, and
the controller changes a target value of a difference between an evaporator outlet piping temperature detected by the evaporator outlet piping temperature detector and an evaporator inlet piping temperature detected by the evaporator inlet fluid temperature detector, according to comparison results of the calculated outlet air dew point temperature with a predetermined target value, and calculates the difference between the evaporator outlet piping temperature and the evaporator inlet piping temperature to control the opening degree of the adjustment valve so that the difference reaches the target value.

5. The indoor unit of claim 2, wherein
the controller calculates a dew point temperature based on an input indoor set temperature and a pre-stored indoor humidity target value to control the opening degree of the adjustment valve so that the detected temperature in the outlet air temperature detector reaches the target value with the dew point temperature being the target value.

6. The indoor unit of claim 2, wherein
the evaporator has a piping arrangement of less than two steps in the same row in a single pass.

7. The indoor unit of claim 2, wherein
a reheat unit in which a condenser is built-in is connected at the downstream side of the air flow in the evaporator.

8. The indoor unit of claim 1, wherein
the controller controls the opening degree of the adjustment valve so that the calculated outlet dew point temperature reaches a predetermined target value.

9. The indoor unit of claim 8, wherein
an evaporator outlet piping temperature detector that detects a fluid temperature at the fluid outlet side of the evaporator is provided, and
the controller changes a target value of a difference between an evaporator outlet piping temperature detected by the evaporator outlet piping temperature detector and an evaporator inlet piping temperature detected by the evaporator inlet fluid temperature detector, according to comparison results of the calculated outlet air dew point temperature with a predetermined target value, and calculates the difference between the evaporator outlet piping temperature and the evaporator inlet piping temperature to control the opening degree of the adjustment valve so that the difference reaches the target value.

10. The indoor unit of claim 8, wherein
the controller calculates a dew point temperature based on an input indoor set temperature and a pre-stored indoor humidity target value to control the opening degree of the adjustment valve so that the detected temperature in the outlet air temperature detector reaches the target value with the dew point temperature being the target value.

11. The indoor unit of claim 8, wherein
the evaporator has a piping arrangement of less than two steps in the same row in a single pass.

12. The indoor unit of claim 8, wherein
a reheat unit in which a condenser is built-in is connected at the downstream side of the air flow in the evaporator.

13. The indoor unit of any of claim 1, wherein
an evaporator outlet piping temperature detector that detects a fluid temperature at the fluid outlet side of the evaporator is provided, and
the controller changes a target value of a difference between an evaporator outlet piping temperature detected by the evaporator outlet piping temperature detector and an evaporator inlet piping temperature detected by the evaporator inlet fluid temperature detector, according to comparison results of the calculated outlet air dew point temperature with a predetermined target value, and calculates the difference between the evaporator outlet piping temperature and the evaporator inlet piping temperature to control the opening degree of the adjustment valve so that the difference reaches the target value.

14. The indoor unit of claim 13, wherein
the controller calculates a dew point temperature based on an input indoor set temperature and a pre-stored indoor humidity target value to control the opening degree of the adjustment valve so that the detected temperature in the outlet air temperature detector reaches the target value with the dew point temperature being the target value.

15. The indoor unit of claim 1, wherein
the controller calculates a dew point temperature based on an input indoor set temperature and a pre-stored indoor humidity target value to control the opening degree of the adjustment valve so that the detected temperature in the outlet air temperature detector reaches the target value with the dew point temperature being the target value.

16. The indoor unit of any of claim 1, wherein the evaporator has a piping arrangement of less than two steps in the same row in a single pass.

17. The indoor unit of any of claim 1, wherein a reheat unit in which a condenser is built-in is connected at the downstream side of the air flow in the evaporator.

18. An air-conditioning apparatus in which the indoor unit of claim 1 is connected with a heat source unit having a compressor, wherein
the controller controls the drive frequency of the compressor so that the calculated outlet dew point temperature reaches a predetermined target value.

19. The air-conditioning apparatus of claim 18, wherein the controller calculates a dew point temperature based on an input indoor set temperature and a pre-stored indoor humidity target value to control the drive frequency of the compressor so that the detected temperature in the outlet air temperature detector reaches the target value with the dew point temperature being a target value.

* * * * *